United States Patent [19]

Wallach

[11] Patent Number: 5,023,086

[45] Date of Patent: * Jun. 11, 1991

[54] ENCAPSULATED IONOPHORE GROWTH FACTORS

[75] Inventor: Donald F. H. Wallach, Brookline, Mass.

[73] Assignee: Micro-Pak, Inc., Wilmington, Del.

[*] Notice: The portion of the term of this patent subsequent to Mar. 27, 2007 has been disclaimed.

[21] Appl. No.: 287,108

[22] Filed: Dec. 20, 1988

Related U.S. Application Data

[63] Continuation-in-part of Ser. No. 157,571, Mar. 3, 1988, Pat. No. 4,911,928, which is a continuation-in-part of Ser. No. 25,525, Mar. 13, 1987, abandoned, and a continuation-in-part of Ser. No. 78,658, Jul. 28, 1987, Pat. No. 4,855,090, and a continuation-in-part of Ser. No. 124,824, Nov. 24, 1987, Pat. No. 4,917,951.

[51] Int. Cl.$^5$ .................... A61K 9/127; A61K 37/36; B01J 13/02
[52] U.S. Cl. .................... 424/450; 264/4.1; 428/402.2; 530/399; 935/13
[58] Field of Search ............. 264/4.1; 428/402.2; 424/450; 530/399; 935/13

[56] References Cited

U.S. PATENT DOCUMENTS

| | | | |
|---|---|---|---|
| 3,372,201 | 3/1968 | Leary et al. | 252/DIG. 1 |
| 3,957,971 | 5/1976 | Oleniacz | 424/70 |
| 4,133,874 | 1/1979 | Miller et al. | 428/402.2 X |
| 4,182,330 | 1/1980 | Michaels | 128/260 |
| 4,217,344 | 8/1980 | Vanlerberghe et al. | 424/60 |
| 4,235,871 | 11/1980 | Papahadjopoulos et al. | 424/450 |
| 4,241,046 | 12/1980 | Papahadjopoulos et al. | 424/450 |
| 4,247,411 | 1/1981 | Vanlerberghe et al. | 264/4.6 |
| 4,279,894 | 7/1981 | Davies et al. | 435/169 X |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,544,545 | 10/1985 | Ryan et al. | 424/1.1 |
| 4,551,288 | 11/1985 | Kelly | 264/4.6 |
| 4,560,665 | 12/1985 | Nakae et al. | 436/172 |
| 4,564,599 | 1/1986 | Janoff et al. | 436/507 |
| 4,603,044 | 7/1986 | Geho et al. | 428/402.2 X |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,708,861 | 11/1987 | Popescu et al. | 424/1.1 |
| 4,721,612 | 1/1988 | Janoff et al. | 424/1.1 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,753,788 | 6/1988 | Gamble | 424/1.1 |
| 4,772,471 | 9/1988 | Vanlerberghe et al. | 424/450 |
| 4,855,090 | 8/1989 | Wallach | 264/4.1 |
| 4,867,980 | 9/1989 | Edwards et al. | 424/468 X |
| 4,911,928 | 3/1990 | Wallach | 424/450 |
| 4,917,951 | 4/1990 | Wallach | 428/402.2 |

FOREIGN PATENT DOCUMENTS

| | | |
|---|---|---|
| 0032578 | 7/1984 | European Pat. Off. |
| 0167825 | 1/1986 | European Pat. Off. |
| 3410602 | 9/1984 | Fed. Rep. of Germany |
| 59-106423 | 6/1984 | Japan |
| 61-207324 | 9/1986 | Japan |
| WO85/01440 | 4/1985 | PCT Int'l Appl. |
| WO87/06499 | 11/1987 | PCT Int'l Appl. |
| 929408 | 6/1963 | United Kingdom |
| 1539625 | 1/1979 | United Kingdom |
| 2078543A | 1/1982 | United Kingdom |
| 2079179A | 1/1982 | United Kingdom |
| 2147263 | 5/1985 | United Kingdom |
| 2198947 | 6/1988 | United Kingdom |

OTHER PUBLICATIONS

*Diffusion of Univalent Ions Across the Lamellae of Swollen Phospholipids,* A. Bingham, et al., J. Mol. Biol. 13, 238–252 (1965).

*McCutcheon's Detergents & Emulsifiers* 1973 North American Edition, p. 27.

*The Carrier Potential of Liposomes in Biology and Medicine* (First of Two Parts), G. Gregoriadis, The New England Journal of Medicine, 295, 704–710 (1976).

*Procedure for Preparation of Liposomes with Large Internal Acqueous Space and High Capture by Reverse-Phase Evaporation,* F. Szoka, Jr. et al., Proc. Natl. Acad. Sct. USA 75, 4194–4198 (1978).

2. *Methodes de Preparation des Liposomes,* N. Douseet, et al., Puisieux and Delattre, Eds. Techniques et Documentation La Voisier Paris, pp. 41–72, (1985).

*McCutcheon's Emulsifiers & Detergents* 1982 North American Edition, pp. 76–77.

*Liposomes,* edited by Marc J. Ostro, The Liposome Co., Princeton, N.J., Marcel Dekker, Inc., New York and Basel, pp. 246–249 (1983).

*A Very Mild Method Allowing the Encapsulation of Very High Amounts of Macromolecules into Very Large (1000 nm) Unilamellar Liposomes,* Philippot, et al., Biochem. Biophys. Acta, 734, 137–143 (1983).

*Bilayer Fluidity of Non–Ionic Vesicle. An Investigation by Differential, Polarized Phase Fluorometry,* A. Ribier, et al., Colloids and Surfaces 10, 155–161 (1984).

(List continued on next page.)

Primary Examiner—Richard D. Lovering
Attorney, Agent, or Firm—Lahive & Cockfield

[57] ABSTRACT

Encapsulated ionophore growth factors and methods of encapsulating these growth factors in lipid vesicles, particularly nonphospholipid paucilamellar lipid vesicles, have been discovered. These methods allow aqueous-based formulations of water-insoluble growth factors to be made.

19 Claims, No Drawings

OTHER PUBLICATIONS

*The Preparation and Properties of Niosomes—Non-Ionic Surfactant Vesicles*, A. Baillie, et al., J. Pharm. Pharmacol., 37, 863–888 (1985).

11. *Les Niosomes*, R. Handjani-Vila, et al., Les Liposomes, Puisieux and Delattre, Eds. Techniques et Documentation La Voisier Paris, pp. 297–313 (1985).

*Extemporaneous Preparation of Large Unilammelar Liposomes*, J. Philippot, et al., Biochem. Biophys. Acta, 821, 79–84 (1985).

*Problemes technologiques poses par l'utilisation des liposomes comme vecteurs de substances medicamenteuses. Encapsulation, Sterilisation, Conservation*, F. Puisieux, et al., Les Liposomes, Ed. Techniques et Documentation La Voisier Paris, pp. 73–113 (1985).

*Non-Ionic Surfactant Vesicles, Niosomes, as a Delivery System for the Anti-Leishmanial Drug, Sodium Stibogluconate*, A. Baillie, et al., J. Pharm. Pharmacol., 38, 502–505, (1986).

ENCAPSULATED IONOPHORE GROWTH FACTORS

REFERENCE TO RELATED APPLICATIONS

This application is a continuation-in-part of U.S. patent application Ser. No. 157,571, filed Mar. 3, 1988, entitled "Paucilamellar Lipid Vesicles," now U.S. Pat. No. 4,911,928, which is a continuation-in-part of U.S. patent application Ser. No. 025,525, filed Mar. 13, 1987, entitled "Method of Producing High Aqueous Volume Multilamellar Vesicles", now abandoned; U.S. patent application Ser. No. 078,658, filed July 28, 1987, also entitled, "Method of Producing High Aqueous Volume Multilamellar Vesicles", now U.S. Pat. No. 4,855,090; and U.S. patent application Ser. No. 124,824, filed Nov. 24, 1987, entitled "Lipid Vesicles Formed of Surfactants and Steroids", now U.S. Pat. No. 4,917,951. The present application is also related to U.S. patent application Ser. No. 163,806, filed Mar. 3, 1988 and now U.S. Pat. No. 4,895,452, entitled "Method and Apparatus for Producing Lipid Vesicles." The disclosures of all of these applications are incorporated herein by reference.

BACKGROUND OF THE INVENTION

The present invention relates to aqueous-based formulations of ionophore growth factors. More particularly, disclosed are encapsulated ionophore growth factors, a method of their production, and methods of treatment using encapsulated ionophores. The ionophore growth factors are encapsulated within nonphospholipid lipid vesicles which are themselves dispersed or suspended in an aqueous-based solution.

Ionophore growth factors are primarily macrolide antibiotics that attack a variety of Gram-negative bacteria and increase growth rate, particularly of ruminant animals. The ionophores are active in ruminants by reducing the proportion of methane produced by ruminal fermentation and increasing the proportion of proprionic acid in the bovine rumen fluid. Most of the ionophore growth factors are substantially water-insoluble so that a formulation which allows the ionophore to be administered in the drinking water of poultry, cattle, or pigs would be highly beneficial. The water-insoluble nature of these ionophore growth factors makes it difficult to encourage the animals to obtain sufficient concentrations of the growth factors by current administration methods, e.g., as a coating on foodstuffs. Even if a sufficient level is attained, this will vary widely on a day-to-day basis depending on the amount of fluid consumed by the animal. However, most animals drink substantially constant amounts of liquid so that an aqueous-based formulation which can be incorporated into the drinking water would give a more constant level of the ionophore. The constant level is of some importance when the macrolides are used as a growth enhancer, e.g., in the treatment of animal growth but is of paramount importance when the antibiotic properties, e.g., anti-swine dysentery activity, are most significant.

Current ionophore growth factor compositions are primarily coating on feed, e.g., cereal products, as well as other grains and grasses. In addition, slow release, intra-ruminal pellets or boluses have been tried to give proper dosages to animals. For example, see U.S. Pat. No. 4,279,894, issued July 21, 1981. However, although the use of liquid carriers have been contemplated, the water-insoluble properties of most ionophore growth factors have made this an unrealistic possibility. Therefore, a carrier of the ionophore growth factor is necessary for aqueous formulations.

Lipid vesicles have not been considered particularly good carriers for water-insoluble materials such as ionophore growth factors because their cost has been too high for use in animal feed and the instability of the lipid vesicles when carrying large quantities of lipophilic material. Lipid vesicles are substantially spherical structures made of materials having a high lipid content, e.g., surfactants or phospholipids. The lipids of these spherical vesicles are organized in the form of lipid bilayers. The lipid bilayers encapsulate an aqueous volume which is either interspersed between multiple onion-like shells of lipid bilayers (forming multilamellar lipid vesicles or "MLV") or the aqueous volume is contained within an amorphous central cavity. The most commonly known lipid vesicles having an amorphous central cavity filled with aqueous medium are the unilamellar lipid vesicles. Large unilamellar vesicles ("LUV") generally have a diameter greater than about $1\mu$ while small unilamellar lipid vesicles ("SUV") generally have a diameter of less than $0.2\mu$. There are a variety of uses for lipid vesicles including the use as adjuvants or as carriers for a wide variety of materials.

Although substantially all the investigation of lipid vesicles in recent years has centered on multilamellar and the two types of unilamellar lipid vesicles, a fourth type of lipid vesicle, the paucilamellar lipid vesicle ("PLV"), exists. This lipid vesicle has barely been studied heretofore and has only been manufactured previously with phospholipids. PLV's consist of about 2 to 10 peripheral bilayers surrounding a large, unstructured central cavity. In all the previously described PLV's, this central cavity was filled with an aqueous solution. See Callo and McGrath, Cryobiology 1985, 22(3), pp. 251–267.

Each type of lipid vesicle appears to have certain uses for which it is best adapted. For example, MLV's have a higher lipid content than any of the other lipid vesicles so to the extent that a lipid vesicle can carry a lipophilic material in the bilayers without degradation, MLV's have been deemed more advantageous then LUV's or SUV's for carrying lipophilic materials. In contrast, the amount of water encapsulated in the aqueous shells between the lipid bilayers of the MLV's is much smaller than the water which can be encapsulated in the central cavity of LUV's, so LUV's have been considered advantageous in transport of aqueous material. However, LUV's, because of their single lipid bilayer structure, are not as physically durable as MLV's and are more subject to enzymatic degradation. SUV's have neither the lipid or aqueous volumes of the MLV's or LUV's but because of their small size have easiest access to cells in tissues.

PLV's, which can be considered a sub-class of the MLV's, are a hybrid having features of both MLV's and LUV's. PLV's appear to have advantages as transport vehicles for many uses as compared with the other types of lipid vesicles. In particular, because of the large unstructured central cavity, PLV's are easily adaptable for transport of large quantities of aqueous-based materials. Also as illustrated in previously cited U.S. patent application Ser. No. 157,571 now U.S. Pat. No. 4,911,928, the aqueous cavity of the PLV's can be filled wholly or in part with an apolar oil or wax and then can be used as a vehicle for the transport or storage of hydrophobic materials. The amount of hydrophobic material which can be transported by the PLV's with an apolar core is much greater than can be transported by MLV's. The multiple lipid bilayers of the PLV's provides PLV's with additional capacity to transport lipophilic material in their bilayers as well as with additional physical strength and resistance to degradation as compared with the single lipid bilayer of the LUV's.

All of the early lipid vesicle or liposome studies used phospholipids as the lipid source for the bilayers. The reason for this choice was that phospholipids are the principal structural components of natural membranes. However, there are many problems using phospholipids as artificial membranes. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the lipid structure breaks down, causing premature release of encapsulated materials and the formation of toxic peroxidation byproducts. This problem can be avoided by hydrogenation but hydrogenation is an expensive process, thereby raising the cost of the starting materials. Cost is a third problem associated with the use of phospholipids on a large scale. A kilogram of egg yolk lecithin pure enough for pharmacological liposome production presently costs in excess of $1,000. This is much to high a cost for a starting material for most applications. Even less highly purified phospholipids are too expensive for most animal uses.

Recently, there has been some indication, particularly from L'Oreal and Micro Vesicular Systems, Inc., that commercially available surfactants might be used to form the lipid bilayer in liposome-like multilamellar lipid vesicles. Both surfactants and phospholipids are amphiphiles, having at least one lipophilic acyl or alkyl group attached to a hydrophilic head group. The head groups are attached to one or more lipophilic chains by ester or ether linkages. Commercially available surfactants include the Brij family of polyoxyethylene acyl ethers, the SPAN sorbitan alkyl esters, and the TWEEN polyoxyethylene sorbitan fatty acid esters, all available from ICI Americas, Inc. of Wilmington, Del.

The methods and materials disclosed herein for producing the paucilamellar lipid vesicles all yield vesicles with a high aqueous or oil volume. Electron micrographs confirm that the paucilamellar lipid vesicles are distinct from the LUV's and the classic MLV's.

Accordingly, an object of the invention is to provide an aqueous-based formulation of an ionophore growth factor.

Another object of the invention is to provide a formulation having factor encapsulated within a nonphospholipid vesicle.

A further object of the invention is to provide a method of preparing an aqueous-based formulation of a substantially water-insoluble ionophore growth factor which exhibit both growth promoting and antibiotic action.

A still further object of the invention is to provide a method of treatment of animals to enhance growth and provide antibiotic action.

These and other objects and features of the invention will be apparent from the following description.

SUMMARY OF THE INVENTION

The present invention features aqueous-based formulations having an ionophore growth factor encapsulated in nonphospholipid lipid vesicles. The invention further features a method of preparing the vesicles and a method of treating animals to enhance growth and provide antibiotic action using the vesicles of the invention.

The aqueous-based formulation of the invention contains at least one active agent selected from a group consisting of ionophore growth factors, and mixtures, derivatives and analogs thereof, encapsulated in lipid vesicles which have nonphospholipid materials as their primary lipid source. The lipid vesicles are dispersed in an aqueous-based carrier. As used herein, the term "disperse" means, includes and implies dispersions, suspensions, colloids, and other similar non-dissolved states. Preferred nonphospholipid materials include lipid vesicle forming polyoxyethylene fatty esters, polyoxyethylene fatty acid ethers, diethanolamines, long-chain acyl amides, long-chain acyl amino acid amides, long-chain acyl amides, polyoxyethylene sorbitan oleates, polyoxyethylene glycerol monostearates, glycerol monostearates, and mixtures, analogs, and derivatives thereof. The vesicles may also include a steroid, and a charge producing agent. Preferred steroids include cholesterol, hydrocortisone, and analogs, derivatives, and mixtures thereof. Preferred negative charge producing materials are oleic acid, dicetyl phosphate, palmitic acid, cetyl sulphate, retinoic acid, phosphatidic acid, phosphatidyl serine, and mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. A preferred positive charge producing material is hexadecyl trimethylammonium bromide, a potent disinfectant. The use of this disinfectant as the positive charge producing material within the vesicles provides a secondary advantage as the vesicles deteriorate; they act as a sustained release germicide carriers.

Although any type of lipid vesicle which could carry sufficient quantities of the water-insoluble ionophore growth factor could be used, paucilamellar lipid vesicles are the most practical choice. These vesicles provide a large, amorphous central transport cavity. The ionophore growth factor can be dissolved or dispersed in a water immiscible oily material which can be used as a carrier for the ionophore. As used herein, the term "water immiscible oily material" means, includes and comprises oils and waxy-like material preferably selected from a group consisting of oils, waxes, natural and synthetic triglycerides, acyl esters, and petroleum derivatives, and their analogs and derivatives.

Preferred ionophore growth factors are water-insoluble, preferably macrolide antibiotics or mixtures, derivatives, or analogs thereof. Preferred water-insoluble ionophore growth factors are selected from a group consisting of tetronasin, monensin, salinomycin, lasolocids, lysocellin, ladlomycin, narosin, and mixtures, derivatives, and analogs thereof. The formulation can include a single ionophore growth factor or a plurality of ionophore growth factors, each encapsulated in lipid vesicles, can be mixed to form a formulation having broad spectrum antibiotic properties.

The formulation is made by dispersing the ionophore containing vesicle in an aqueous-based solution. A substantially water-insoluble ionophore growth factor is encapsulated in a nonphospholipid lipid vesicles. The lipid vesicles are made by forming a lipophilic phase of nonphospholipid materials combined with any other lipophilic materials which are to be encapsulated, combining the water-insoluble ionophore growth factor with a water immiscible oily material, dispersing the water immiscible oily material containing the ionophore growth factor in the lipophilic phase, forming an aqueous phase of aqueous soluble materials to be encapsulated in the lipid vesicle by dispersing the aqueous soluble materials in an aqueous carrier, and shear mixing the lipophilic phase and the aqueous phase to form lipid vesicles. "Shear mixing" means, includes and implies the mixing of the lipophilic phase with the aqueous phase under turbulent or shear conditions which provide adequate mixing to hydrate the lipid and form lipid vesicles. In many instances, calibrated metering pumps are used to drive the phases to form the vesicles. The pump speeds for mixing the phases are modified depending on the viscosity of the materials and the size of the orifices selected. "Shear mixing" is achieved by liquid shear which is substantially equivalent to a relative flow rate for the combined phases of about 5–30 m/s through a 1 mm radius orifice.

All of the lipid materials useful in forming the vesicles of the invention can be classified as surfactants. However, standard methods of manufacture, although they may be used, are not as efficient as those set forth herein. In order to achieve the proper blending necessary to form the paucilamellar lipid vesicles, all of the materials are normally in a flowable state. However, in the process of the present invention, use of a solvent for the surfactant (the classic method of producing multilamellar lipid vesicles) is not only unnecessary; it is counter-productive. Many of the surfactants useful in the invention are liquids at room temperature or at slightly elevated temperatures so only gentle heating is necessary for flowability. Even the most difficult surfactants of the group to use, e.g., glycerol monostearate, can be easily handled at approximately 70° C. Therefore, one standard procedure of the invention is to elevate the temperature of the lipophilic phase in order to make it flowable followed by carrying out the shear mixing between the lipophilic phase and the aqueous phase at a temperature such that both phases are liquids. While it is often desirable to use the same temperature for both phases, this is not always necessary.

The formulation of the invention can be used as a treatment to enhance growth and to provide antibiotic action in animals. The ionophore growth factors exhibit both actions simultaneously, making them efficient materials to use on animals. However, the invention is not limited to cases where both effects of the ionophore growth factors are equally pertinent but rather all circumstances where the ionophore growth factors are used for treatment as either an antibiotic or a growth promoter.

The invention will be further understood by the following description and the Examples.

DESCRIPTION OF THE INVENTION

The present invention solves a number of the problems of using ionophore growth factors because of the ability to make aqueous-based formulations. The ability to add ionophore growth factors to drinking water yields a much easier method of treating the animals than those presently used.

The preferred lipid vesicles are paucilamellar lipid vesicles having a water immiscible oily material within the amorphous central cavity. The water immiscible oily material can act as a carrier for the water-insoluble ionophore.

Although any lipid vesicle forming material could, theoretically, be used to form the lipid vesicles of the invention, the most preferred surfactants useful in the invention are selected from a group consisting of polyoxyethylene fatty esters having the formula $$R_1—COO(C_2H_4O)_nH$$

where $R_1$ is lauric, myristic, cetyl, stearic, or oleic acid, or their derivatives and $n=2-10$;
polyoxyethylene fatty acid ethers, having the formula $$R_2—CO(C_2H_4O)_mH$$

where $R_2$ is lauric, myristic, or cetyl acids or their derivatives, single or double unsaturated octadecyl acids or their derivative, or double unsaturated eicodienoic acids or their derivatives and m ranges from 2–4;
diethanolamines, having the formula $$(HOCH_2—CH_2)_2NCO—R_3$$

where $R_3$ is caprylic, lauric, myristic or linoleic acids or their derivatives;
long chain acyl hexosamides having the formula $$R_4—NOCO—(CH_2)_b—CH_3$$

where b ranges from 10–18 and $R_4$ is a sugar molecule selected from a group consisting of glucosamine, galactosamine, and N-methylglucamine;
long chain acyl amino acid amides having the formula $$R_5—CHCOOH—NOC—(CH_2)_c—CH_3$$

where c ranges from 10–18 and $R_5$ is an amino acid side chain;
long chain acyl amides having the formula $$HOOC—(CH_2)_d—N(CH_3)_2—(CH_2)_3—NCO—R_6$$

where $R_6$ is an acyl chain having 12–20 carbons and not more than two unsaturations, and d ranges from 1–3;
polyoxyethylene (20) sorbitan mono- or trioleate;
polyoxyethylene glyceryl monostearate with 1–10 polyoxyethylene groups; and glycerol monostearate.

The paucilamellar lipid vesicles can be made by a variety of devices which provides sufficiently high shear for shear mixing. There are a large variety of these devices available on the market including a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, N.J. and is further described in previously cited U.S. patent application Ser. No. 163,806, and now U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. In a preferred embodiment, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

The invention, and its uses, will be further explained by the following Examples.

EXAMPLE 1

A series of formulations were made by encapsulating tetronasin, an ionophore growth factor, in lipid vesicles and suspending the tetronasin filled vesicles in water to make the formulation of the invention. Two methods were used to make the vesicles; one using relatively large scale amounts uses the Micro Vesicular Systems previously described and the second, a test system, used two syringes connected by a stopcock. The same proportions of material were used in all the formulations, but modifications were made in certain of the ingredients.

The first formulation tested was a test system made by a syringe method. Approximately 0.5 g of tetronasin is dissolved in 5 ml of Drakeol 19 (mineral oil USP) which is heated to approximately 40° C. until a clear solution develops. The tetronasin forms approximately 2% of the final preparation while the mineral oil forms approximately 27%. The mineral oil can be replaced by a different oil, e.g., peanut oil, which work equally as well. The water-immiscible oil-tetronasin is blended with a lipid vesicle-forming stock solution containing polyoxyethylene 2-cetyl ether (Brij 52-ICI Americas, Inc.), cholesterol, and oleic or palmitic acid in a ratio of 33/11/1.5. The total amount of the lipid vesicle-forming stock solution used is approximately one-half of the mineral oil volume. At 40° C., the lipid solution and the oil solution form a clear solution. The solution may then be filtered through a 5μ filter for further clarification. The lipid phase is then hydrated, using approximately an eight fold excess of water. Hydration is carried out by shooting the solutions back and forth from syringes through a stopcock for about two minutes. Alternatively, a device such as the Micro Vesicular Systems lipid vesicle forming machine or could be used. Uniform lipid vesicles having a diameter of approximately 1-2μ having an oily center filling the amorphous center cavity are formed.

To test stability, the lipid vesicles were centrifuged for approximately 20 minutes at 3,000 rpm without a dextran layer. No sediment was seen. Approximately five days later, the same centrifuge test was carried out, also yielding no sediment. No sediment developed after a 10,000 rpm centrifuge test.

The final proportions used are set forth in Table 1.

TABLE 1

|  | % w/v |
| --- | --- |
| TETRONASIN | 2.00 |
| Brij 52 | 16.24 |
| CHOLESTEROL | 5.06 |
| OLEIC ACID | 0.70 |
| MINERAL OIL | 27.20 |
| WATER TO | 100 cm$^3$ |

The final concentration of tetronasin was approximately 2% by weight.

EXAMPLE 2

Tetronasin is known to have antibiotic effect against *Treponema hyodysenteriae* infection in pigs, the causative organism in swine dysentery. Although aqueous-based solutions of tetronasin have been tried, the very low aqueous solubility has made this an ineffective method of treatment. Accordingly, a lipid vesicle preparation made as described in Example 1 was tried for efficacy against swine dysentery. A series of pigs were offered water containing approximately 60 mg/l tetronasin in the formulation of Example 1, using mineral oil as the internal carrier. There was a slow regression of the dysentery symptoms but the treatment was generally effective. However, water intake of the pigs was approximately half that of the control group, showing that the pigs either did not like the lipid vesicles or the tetronasin itself. Addition of an artificial flavor to the water assisted somewhat in increasing water uptake and improve the response of the pigs, but water uptake was still lower than a control group.

In order to determine whether the pigs objected to the flavor of the lipid vesicle or the tetronasin, one group of pigs were offered water containing approximately 2.9 g/l of lipid vesicles without tetronasin. Water uptake was compared with a control group given water without the vesicles. There was substantially no difference in water uptake, showing that the tetronasin was the material objected to by the pigs. To confirm this, the pigs were offered water containing lipid vesicles without tetronasin and with tetronasin. The pigs receiving the tetronasin drank only about 40% of the others, confirming that the taste or smell of the tetronasin was objected to by the pigs.

Replacing the mineral oil with a peanut oil to improve palatability of the tetronasin solution showed little improvement. However, it is believed formulations can be made which mask the tetronasin taste problem and provide adequate protection to the test animals. All the formulations showed antibiotic action.

The foregoing Examples are expressly non-limiting and are merely to show the efficacy of the present invention. The invention is defined by the following claims.

What is claimed is:

1. An aqueous-based formulation active to promote animal growth comprising at least one active agent selected from a group consisting of substantially water insoluble ionophore growth factors, and mixtures thereof encapsulated in the amorphous central cavity of paucilamellar lipid vesicles dispersed in an aqueous-based carrier, said lipid vesicles having a nonphospholipid material as their primary lipid source.

2. The formulation of claim 1 wherein said nonphospholipid material is selected from a group consisting of lipid vesicles forming polyoxyethylene fatty esters, polyoxyethylene fatty acid ethers, diethanolamines, long chain acyl hexosamides, long chain acyl amino acid amides, long chain acyl amides, glycerol monostearates, and mixtures thereof.

3. The formulation of claim 2 wherein said lipid vesicles further comprise a steroid.

4. The formulation of claim 3 wherein said steroid is selected from a group consisting of cholesterol, hydrocortisone, and mixtures thereof.

5. The formulation of claim 1 wherein said lipid vesicle further comprises a charge-producing agent.

6. The formulation of claim 1 wherein said lipid vesicle further comprises a water immiscible oily material enclosed in the amorphous central cavity of said paucilamellar lipid vesicles, said water-immiscible oily material acting as a carrier for said ionophore growth factor.

7. The formulation of claim 6 wherein said ionophore growth factor is water insoluble.

8. The formulation of claim 7 wherein said ionophore growth factor comprises a macrolide antibiotic or a mixture thereof.

9. The formulation of claim 8 where said water insoluble ionophore growth factor is selected from a group consisting of tetronasin, monensin, salinomycin, lasolocids, lysocellin, ladlomycin, narosin, and mixtures thereof.

10. The formulation of claim 1 wherein said formulation comprises a plurality of ionophore growth factors, each of said ionophore growth factors being encapsulated in a separate lipid vesicle.

11. A method of preparing an aqueous-based formulation exhibiting growth promoting and antibiotic action in animals, said formulation having a substantially water insoluble ionophore growth factor encapsulated in the amorphous central cavity of paucilamellar lipid vesicles dispersed in an aqueous-based solution, said lipid vesicles having a nonphospholipid material as its primary lipid source, said method comprising the steps of:
  a. Forming a lipophilic phase of said nonphospholipid materials combined with any other lipophilic materials to be encapsulated therein;
  b. Combining said water insoluble ionophore growth factor with a water immiscible oily material;
  c. Dispersing said water immiscible oily material containing said ionophore growth factor in said lipophilic phase;
  d. Forming an aqueous phase of aqueous soluble materials to be encapsulated in said lipid vesible, said aqueous soluble materials being dispersed in an aqueous carrier; and
  e. Shear mixing said lipophilic phase and said aqueous phase to form said lipid vesicles.

12. The method of claim 11 wherein said nonphospholipid material is selected from a group consisting of lipid vesicles forming polyoxyethylene fatty esters, polyoxyethylene fatty acid ethers, diethanolamines, long chain acyl hexosamides, long chain acyl amino acid amides, long chain acyl amides, glycerol monostearates, and mixtures thereof.

13. The method of claim 11 wherein said water insoluble ionophore growth factor comprises a macrolide antibiotic or a mixture thereof.

14. The method of claim 13 wherein said water insoluble ionophore growth factor is selected from a group consisting of tetronasin, monesin, salinomycin, lasolocids, lysocellin, ladlomycin, narosin, and mixtures thereof.

15. A method of treatment to enhance growth and provide antibiotic action in animals comprising the step of treating the animal with an aqueous-based formulation of an ionophore growth factor, said aqueous based formulation having a water insoluble ionophore growth factor encapsulated in the amorphous central cavity of a paucilamellar liquid vesicle dispersed in an aqueous solution, said lipid vesicle having a nonphospholipid as its primary lipid source.

16. The method of claim 15 wherein said water insoluble ionophore growth factor is dispersed in a water immiscible oily material which is encapsulated in said lipid vesicles.

17. The method of claim 15 wherein said nonphospholipid material is selected from a group consisting of lipid vesicles forming polyoxyethylene fatty esters, polyoxyethylene fatty acid ethers, diethanolamines, long chain acyl hexosamides, long chain acyl amino acid amides, long chain acyl amides, glycerol monostearates, and mixtures thereof.

18. The method of claim 15 wherein said water insoluble ionophore growth factor comprising a macrolide antibiotic, or a mixture thereof.

19. The method of claim 18 wherein said ionophore growth factor is selected from a group consisting of tetronasin, monensin, salinomycin, lasolocids, lysocellin, ladlomycin, narosin and mixtures thereof.

* * * * *

UNITED STATES PATENT AND TRADEMARK OFFICE
CERTIFICATE OF CORRECTION

PATENT NO. : 5,023,086
DATED : June 11, 1991
INVENTOR(S) : Donald F.H. Wallach

It is certified that error appears in the above-identified patent and that said Letters Patent is hereby corrected as shown below:

Column 10, line 2, replace "vesible" with --vesicle--.

Signed and Sealed this

Third Day of May, 1994

Attest:

BRUCE LEHMAN

*Attesting Officer*    *Commissioner of Patents and Trademarks*